United States Patent [19]

Paulos et al.

[11] Patent Number: 4,988,351
[45] Date of Patent: Jan. 29, 1991

[54] WASHER FOR USE WITH CANCELLOUS SCREW FOR ATTACHING SOFT TISSUE TO BONE

[75] Inventors: Leon E. Paulos; Thomas D. Rosenberg, both of Salt Lake City, Utah; Randall D. Ross, Largo, Fla.

[73] Assignee: Concept, Inc., Largo, Fla.

[21] Appl. No.: 293,973

[22] Filed: Jan. 6, 1989

[51] Int. Cl.⁵ .............................................. A61F 5/04
[52] U.S. Cl. ....................................... 606/72; 606/75
[58] Field of Search ............... 411/531, 539, 546, 545; 128/92 YE, 92 YF, 92 YK; 606/72, 75

[56] References Cited

U.S. PATENT DOCUMENTS

| | | | |
|---|---|---|---|
| 937,199 | 10/1909 | Willard | 411/531 |
| 2,490,364 | 12/1949 | Livingston | 128/92 YK |
| 2,570,465 | 8/1949 | Lundholm | 606/65 |
| 2,765,787 | 10/1956 | Pellet | 128/92 YF |
| 3,212,387 | 10/1965 | Madansky | 411/546 |
| 3,554,193 | 1/1971 | Konstantinou | 606/65 |
| 3,579,831 | 5/1971 | Stevens et al. | 433/174 |
| 3,596,656 | 8/1971 | Kaute | 606/71 |
| 3,761,867 | 9/1973 | Churla | 411/539 |
| 3,875,936 | 4/1975 | Volz | 128/92 YF |
| 3,997,138 | 12/1976 | Crock et al. | 128/92 YF |
| 4,429,690 | 2/1984 | Angelino-Pievani | 606/69 |
| 4,493,317 | 1/1985 | Klaue | 606/69 |
| 4,688,561 | 8/1987 | Reese | 128/92 YF |
| 4,796,612 | 1/1989 | Reese | 128/92 YF |

OTHER PUBLICATIONS

Synthes Literature "AO Screw", pp. 12, 13, 28 and 29, Anterior Cruciate Ligament Repairs in World Class Skiers, by R. W. Higgins et al, pp. 439–447 *The American Journal of Sports Medicine*, vol. 15, No. 5 1987.
Various AO Literature.

*Primary Examiner*—Robert A. Hafer
*Assistant Examiner*—Charles H. Sam
*Attorney, Agent, or Firm*—Epstein, Edell & Retzer

[57] ABSTRACT

A soft tissue washer for use with a cancellous screw for attaching soft tissue, such as ligaments, to bone has posts disposed on a distal face of a washer body to limit penetration of sharp pins extending from the distal face into soft tissue, an annular recess disposed is the distal face to receive and clamp soft tissue, recess portions deeper than the annular recess disposed in the distal face to relieve compression of soft tissue, a dished recess in a proximal face of the washer body to entirely receive the head of the cancellous screw such that the head does not protrude from the washer and suture retention passages extending from the dished recess to a lateral rim of the washer for receiving sutures.

28 Claims, 1 Drawing Sheet

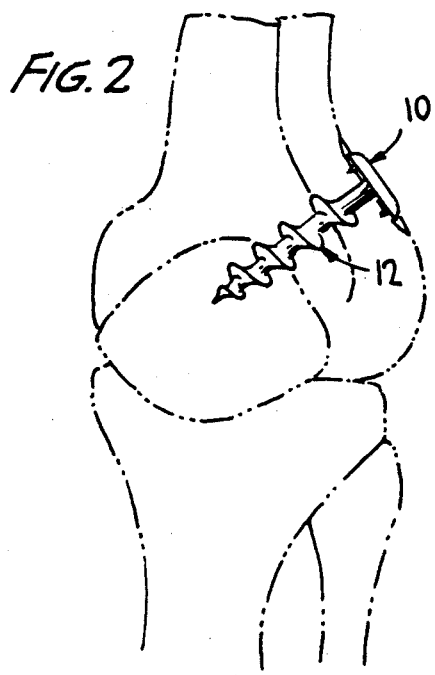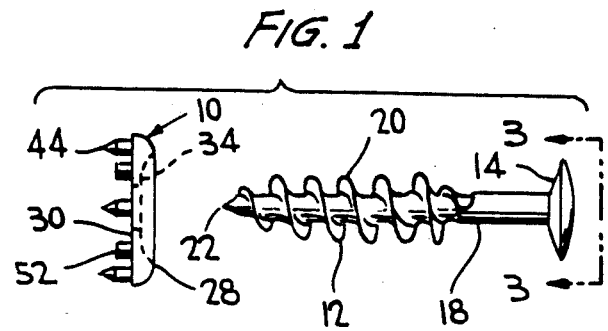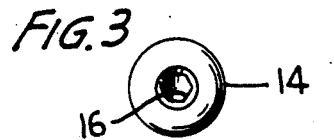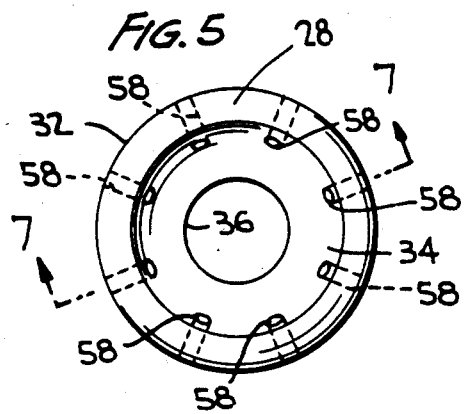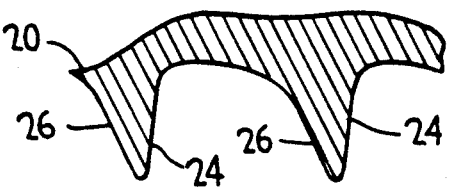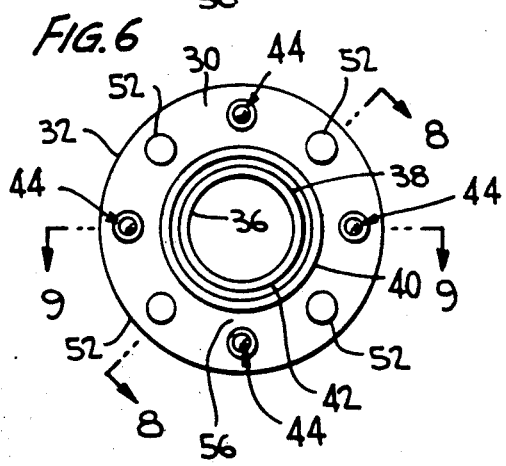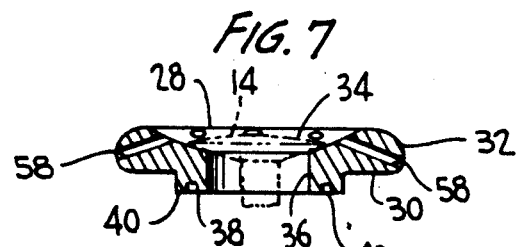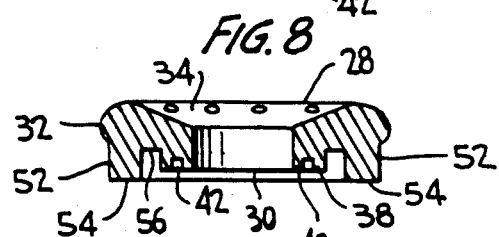

WASHER FOR USE WITH CANCELLOUS SCREW FOR ATTACHING SOFT TISSUE TO BONE

BACKGROUND OF THE INVENTION

1. Field of the Invention:

The present invention pertains to medical devices for securing bodily tissue and, more particularly, to soft tissue washers for use with screws to attach soft tissue to bone.

2. Discussion of the Prior Art:

Soft tissue washers are used with screws for the surgical attachment of soft tissue, such as ligaments, to bone, as described in an article entitled "Anterior Cruciate Ligament Repairs in World Class Skiers" by R. W. Higgins, M.D., et al, The American Journal of Sports Medicine, Vol. 15, No. 6, pp. 439-447, 1987. During surgical procedures to attach soft tissue to bone, such as to attach the anterior cruciate ligament to the femur and as described in the Higgins et al article, a soft tissue washer is used in combination with a cancellous screw such that, when the screw is tightened, the washer penetrates the tissue to contact the bone. Dependent upon the repair required, frequently it is desired to use sutures along with the soft tissue washers.

Prior art soft tissue washers for use with cancellous screws, as exemplified by the "AO" spiked washers and cancellous screws manufactured by Synthes Ltd., have the disadvantages of having relatively high profiles creating obstructions subject to contact with tissue, of not being designed to accommodate sutures, of compressing the soft tissue along the entire distal surface and of easily penetrating the bone at an angle to the perpendicular since all distal protrusions are spiked to permit penetration.

SUMMARY OF THE INVENTION

Accordingly, it is a primary object of the present invention to overcome the disadvantages of the prior art by providing a soft tissue washer for use with a cancellous screw having a configuration to produce a relatively low profile, when used with a cancellous screw, to accommodate sutures, to limit compression of the soft tissue while maintaining secure attachment to the bone and to pivot the washer to a position parallel to the bone surface for optimum alignment.

Another object of the present invention is to provide a curved or dished recess in the proximal face of a soft tissue washer to receive a relatively flat head of a cancellous screw to provide a low profile.

An additional object of the present invention is to arrange a plurality of sharp pins annularly around the distal face of a soft tissue washer to penetrate the soft tissue and to dispose posts between the pins to limit penetration of the pins and, in turn, limit compression of the soft tissue while also causing the washer to be self-leveling to pivot to a position parallel to the bone surface.

The present invention has a further object in that recesses are disposed in the distal face of soft tissue washer to allow soft tissue to flow therein to avoid compression.

Yet another object of the present invention is to provide passages through a soft tissue washer from the proximal face to a lateral rim to receive and retain sutures.

Another object of the present invention is to dispose an annular wall around a central bore in a soft tissue washer to define an annular recess in the distal face of the washer to capture soft tissue.

The present invention is generally characterized in a washer for engaging soft tissue in the body including washer body having a proximal face and a distal face, pins extending from the distal face for penetrating soft tissue, and stop means spaced from the pins and extending from the distal face a distance less than the pins to limit penetration of the pins in the soft tissue. The present invention is further generally characterized in a washer for engaging soft tissue in the body including a washer body having a proximal face and a distal face, pins extending from the distal face for penetrating soft tissue, and an annular recess disposed in the distal face for receiving soft tissue when the pins penetrate the soft tissue. The present invention is further generally characterized in a washer for engaging soft tissue in the body including a washer body having a proximal face, a distal face and a central bore therethrough, pins extending from the distal face for penetrating soft tissue, and passage means extending through the washer body for receiving sutures.

The present invention is additionally characterized in apparatus for attaching soft tissue to bone including a cancellous screw having a threaded shank and a low profile head, and a soft tissue washer including a washer body having a proximal face, a distal face and a central bore therethrough, a plurality of pins extending from the distal face for penetrating soft tissue, a dished recess disposed in the proximal face and passage means passing through the washer body from an opening in the dished recess for receiving sutures, the shank of the cancellous screw passing through the central bore and the head of the cancellous screw being received entirely in the dished recess leaving the opening of the passage means unobstructed.

BRIEF DESCRIPTION OF THE DRAWINGS

FIG. 1 is a side view of the soft tissue washer and cancellous screw of the present invention;

FIG. 2 is a side view of the soft tissue washer and cancellous screw of the present invention used for repair of the anterior cruciate ligament in the knee.

FIG. 3 is a top view of the head of the cancellous screw taken along line 3—3 of FIG. 2.

FIG. 4 is a broken sectional view of the thread of the cancellous screw.

FIG. 5 is top view of the proximal face of the soft tissue washer.

FIG. 6 is a bottom view of the distal face of the soft tissue washer.

FIG. 7 is a section taken along line 7—7 of FIG. 5 showing the suture retention holes.

FIG. 8 is a section taken along line 8—8 of FIG. 6 showing the posts.

FIG. 9 is a section taken along line 9—9 of FIG. 6 showing the sharp pins.

DESCRIPTION OF THE PREFERRED EMBODIMENT

A soft tissue washer 10 and a cancellous lag screw 12 in accordance with the present invention are shown in FIG. 1 and in FIG. 2 for use in repair of the anterior cruciate ligament of the knee, the cancellous screw 12 penetrating the condyle of the femur and passing centrally through the soft tissue washer 10 which penetrates the ligament to attach the ligament to the femur.

The cancellous screw 12 is preferably made of a titanium alloy and has a relatively flat circular head 14 having a hexagonal socket 16 therein to receive a driving tool, as shown in FIG. 3, and a shank 18 carrying threads 20 and terminating at a sharp cone-like distal end 22. The thread 20 spirals outwardly from the distal end and, as shown in FIG. 4, has a side 24 facing head 14 extending from the longitudinal axis of the screw at an angle of approximately 85° to resist removal of the screw while the opposite side 26 of the thread tapers toward the distal end and extends from the longitudinal axis of the screw at an angle of approximately 25° such that the included angle between sides 24 and 26 is approximately 30°. The spacing between identical positions on the threads is preferably 0.108 inches. The side 26 curves into the base of the thread with a radius of curvature of 0.047 inches while the base curves into side 24 with a radius of 0.032 inches. The major diameter of the thread 20 is preferably 0.256 inches (6.5 mm), and the minor diameter of the thread is preferably 0.118 inches. The length of the cancellous screw is dependent upon the bone with which the cancellous screw is to be used, normally in the range of from 0.98 to 1.77 inches, the unthreaded length of shank 18 preferably remaining constant at 0.36 inches. The flat head 14 has an underside having a radius of curvature of 0.394 inches and a flat top slightly curved at the periphery with a radius of 0.187 inches such that the head is shallow having a dimension along the longitudinal axis of the cancellous screw preferably of 0.054 inches.

The soft tissue washer 10 is round, as shown in FIGS. 5 and 6, and is preferably made of a titanium alloy to have an outer diameter of 0.550 inches. The soft tissue washer is formed of a washer body having a proximal face, generally indicated at 28, and a distal face, generally indicated at 30, separated by a curved lateral rim 32. A dished recess 34 is disposed in the proximal face 28 having a curved bottom wall, preferably at a radius of 0.394 inches to mate with the underside of the head 14 of the cancellous screw, a diameter greater than the diameter of the head 14, preferably 0.42 inches, and a depth greater than the longitudinal dimension of the head 14, preferably 0.064 inches, such that the head of the cancellous screw can be entirely received in the recess without protruding therefrom. The washer body preferably has a longitudinal dimension extending along a central axis of 0.80 inches, and the curved lateral rim 32 has a greater radius of curvature adjacent the proximal face 28, preferably 0.060 inches, than adjacent the distal face 30, preferably 0.025 inches. A central bore 36 extends through the washer body to communicate with recess 34 and is defined by a cylindrical wall terminating at a distal edge 38 extending from the distal face 30 to form a rounded annular lip, preferably having a width of 0.015 inches, the cylindrical wall preferably having a length of 0.046 inches such that lip 38 is spaced 0.110 inches from the edge of the proximal face 28. The bore 36 has a diameter less than the major diameter of the thread 20 of cancellous screw 12 but greater than the minor diameter of the thread, preferably 0.210 inches, such that the cancellous screw cannot pass through the washer without relative rotation therebetween. An annular wall 40 extends from the distal face 30 concentrically around lip 38 to define an annular recess 42 therebetween, the wall 40 preferably having an outer diameter of 0.30 inches and a width of 0.015 inches such that the width of annular recess 42 is 0.015 inches.

A plurality of equally spaced, sharp pins 44 are arranged in a circle around the distal face 30 midway between wall 40 and the outer edge of rim 32, four pins 44 being shown in FIG. 6 disposed at 90° intervals. The diameter of the circular arrangement of the centers of the pins is preferably 0.428 inches, and the pins have bases 46 terminating at annular lands 48 from which extend cones 50 tapering to points, as shown in FIG. 9. The bases 46 are preferably cylindrical having diameters of 0.072 inches and lengths to extend beyond lip 38 and wall 40, preferably by 0.02 inches. Cones or spikes 50 preferably have diameters at the widest point of 0.038 inches such that the annular lands have widths of 0.17 inches, and the apex angles of the cones preferably are 50° such that the cones have lengths of 0.04 inches protruding beyond the lands.

A plurality of posts 52 having the same configurations as the bases 46 of pins 44, but with flat faces or lands 54, are equally spaced in a circular arrangement around distal face 40 such that each post is equally spaced between two pins 44. The posts have dimensions identical to the bases 46 of the pins such that the annular lands 48 of the pin bases are aligned with the flat faces or lands 54 of the posts. As shown in FIGS. 8 and 9, the pins and posts are spaced from wall 40 to define recess portions 56 therebetween and between adjacent pins and posts coinciding with distal face 30, the annular recess 42 being shallower than the recess portions and, preferably, having a depth of 0.015 inches, while the recess portions have a greater depth from the edge of wall 40, preferably 0.03 inches.

As best shown in FIGS. 5 and 7, a plurality of suture retention holes or passages 58 are equally spaced around the soft tissue washer and extend angularly through the washer body from openings in the wall of dished recess 34 adjacent the top edge thereof to openings in the lateral rim. Preferably, eight suture retention holes are provided at 45° intervals in alignment with the spaces between adjacent posts and pins, the holes having diameters of 0.037 inches and extending at angles of 60° to the central axis of the soft tissue washer. With the exception of the points of pins 44, all edges or corners of the soft tissue washer are preferably rounded.

In use, the soft tissue washer can be secured to soft tissue, such as a ligament, via sutures passing through the suture retention holes 58 without interfering with seating of the distal face against the tissue; and, as shown in dashed lines in FIG. 7, the head 14 of the cancellous screw is received in the dished recess 34 in the soft tissue washer such that not only does the head not protrude above the washer but the head does not obstruct the openings in the wall of the recess allowing access to the suture retention holes 58. When the soft tissue washer 10 is forced against the tissue by rotation of the cancellous screw 12, the tissue will flow into the annular recess 42 and into the recess portions surrounding the pins 44 and the posts 52. The lands 54 on the posts cooperate with the annular lands 48 on the pins to provide positive stops to limit penetration of the pins and control positioning of the soft tissue washer while tissue compression is limited. Additionally, the posts cannot penetrate the bone but rather act to pivot the washer to a position parallel to the bone surface for alignment. That is, due to the pivoting action of the posts, the washer is self-leveling when the cancellous screw enters the bone at an angle to the perpendicular.

The titanium alloy preferably utilized in forming the soft tissue washer and the cancellous screw is TI-6AL- 4V ELI which has the advantages of good biocompatibility and significant strength when compared to plastic materials, such as polyacetal, allowing the cancellous screw to be torqued to a higher value without danger of breaking the washer, the washer being able to withstand higher loads without deformation or cracking. With the head of the cancellous screw completely buried in the dished recess below the profile of the washer, the opportunity for the occurrence of pain due to the screw/washer combination bearing against soft tissue is minimized. The specific embodiment of the soft tissue washer set forth above has a post height of 1.3 mm; however, the post height can be varied, for example to 2.5 mm, for handling thick tissue reattachments. Since the posts are not positioned at the outer edge of the distal face of the washer, a generous radius on the outer edge of the washer is provided to minimize the danger of tissue snagging on the washer edge, and the bending moment within the washer body is reduced due to a lower moment arm between the screw and the posts producing less stress than if the posts were disposed at the edge of the washer. The sharp pins are designed to easily penetrate the cortical bone and prevent rotation of the washer as the screw is finally tightened while the lands on the posts and at the interface of the base with the conical spike limit the extent to which the washer can be driven into the bone to only the conical spikes. When the washer is compressed by the screw, the lip 38 and the wall 40 compress the tissue tightly in the area of the central bore to provide a tight clamping action while tissue is allowed to flow into the annular recess 42. As the tissue is pulled laterally in tension, the clamped tissue acts like a knot to resist lateral movement. The clamping of the rings formed by lip 38 and wall 40 around the screw minimizes the elongation of pre-existing incisions required in order to insert the screw through the tissue originally. The suture retention holes provide convenient anchoring locations to tie off sutures once the washer is seated.

Inasmuch as the present invention is subject to many variations, modifications and changes in detail, it is intended that the subject matter discussed above and shown in the accompanying drawings be interpreted as illustrative and not in a limiting sense.

What is claimed is:

1. A washer for engaging soft tissue in the body comprising
   a washer body having a proximal face and a distal face;
   pin means extending from said distal face for penetrating soft tissue; and
   stop means independent of said pin means, and laterally spaced from said pin means, said stop means extending from said distal face a distance less than said pin means to limit penetration of said pin means in the soft tissue.

2. A washer as recited in claim 1 wherein said pin means includes a plurality of sharp pins arranged around said distal face.

3. A washer as recited in claim 2 wherein said stop means includes a plurality of posts arranged around said distal face.

4. A washer as recited in claim 3 wherein each of said posts is disposed between two of said pins.

5. A washer as recited in claim 4 wherein said washer body has a circular configuration and has a central bore therethrough, and said pluralities of pins and posts are arranged in a circular configuration around said central bore.

6. A washer as recited in claim 5 wherein said proximal face of said washer body has a dished recess therein communicating with said central bore.

7. A washer as recited in claim 6 and further comprising recess means disposed adjacent said distal face of said washer body for receiving soft tissue when said pins penetrate the soft tissue.

8. A washer as recited in claim 7 wherein said recess means includes an annular recess surrounding said central bore.

9. A washer as recited in claim 8 wherein said washer body includes a lateral rim extending around said dished recess in said proximal face and a plurality of suture retention holes passing through said washer body from openings in said dished recess to openings in said lateral rim.

10. A washer as recited in claim 9 wherein said suture retention holes extend at an angle to the axis of said central bore and are aligned between said posts and pins.

11. A washer as recited in claim 1 and further comprising recess means disposed adjacent said distal face of said washer body for receiving soft tissue when said pins penetrate the soft tissue.

12. A washer as recited in claim 11 wherein said recess means includes an annular recess surrounding said central bore.

13. A washer as recited in claim 1 wherein said washer body has passage means extending therethrough for receiving sutures.

14. A washer as recited in claim 13 wherein said washer body has a lateral rim, said proximal face has a dished recess therein and said passage means extends between said dished recess and said lateral.

15. A washer for engaging soft tissue in the body comprising
   a washer body having a proximal face, a distal face, a bore extending longitudinally through said washer body from said proximal face to said distal face and a wall disposed at said distal face surrounding said bore;
   pin means extending from said distal face for penetrating soft tissue; and
   recess means disposed in said wall for receiving soft tissue when said pin means penetrates the soft tissue.

16. A washer as recited in claim 15 wherein said bore passes centrally through said washer body and said recess means includes an annular recess surrounding said central bore.

17. A washer as recited in claim 16 wherein said pin means includes a plurality of sharp pins arranged around said distal face.

18. A washer as recited in claim 16 wherein said proximal face of said washer body has a dished recess therein communicating with said central bore and said washer body has a lateral rim and passage means extending between said dished recess and said lateral rim for receiving sutures.

19. A washer for engaging soft tissue in the body comprising
   a washer body having a proximal face, a distal face and a central bore therethrough;
   pin means extending from said distal face for penetrating soft tissue; and passage means separate from said central bore extending through said washer body for receiving sutures.

20. A washer as recited in claim 19 wherein said washer body includes a lateral rim and said passage means extends between said proximal face and said lateral rim.

21. A washer as recited in claim 20 wherein said proximal face has a dished recess therein and said passage means includes a plurality of suture retention holes extending between openings in said dished recess and openings in said lateral rim.

22. Apparatus for attaching soft tissue to bone comprising
a cancellous screw having a threaded shank and a low profile head; and
a soft tissue washer including a washer body having a proximal face, a distal face and a central bore therethrough, a plurality of pins extending from said distal face for penetrating soft tissue, a dished recess disposed in said proximal face and passage means passing through said washer body from an opening in said dished recess for receiving sutures,
said shank of said cancellous screw passing through said central bore and said head of said cancellous screw being received entirely in said dished recess leaving said opening of said passage means unobstructed.

23. Apparatus for attaching soft tissue to bone as recited in claim 22 wherein said passage means includes a plurality of suture retention holes passing through said washer body from openings in said dished recess.

24. Apparatus for attaching soft tissue to bone as recited in claim 23 wherein said washer body includes a lateral rim extending around said dished recess and said suture retention holes extend between said dished recess and said lateral rim.

25. Apparatus for attaching soft tissue to bone as recited in claim 24 wherein said distal face of said washer body has an annular recess therein surrounding said central bore for receiving soft tissue when said pins penetrate the soft tissue.

26. Apparatus for attaching soft tissue to bone as recited in claim 25 wherein a plurality of posts extend from said distal face of said washer body a distance less than said pins to limit penetration of said pins in the soft tissue.

27. A device for engaging tissue in the body comprising
a body having a proximal face and a distal face;
a plurality of spaced sharp pins extending from said distal face; and
a plurality of posts independent of said pins extending from said distal face and spaced from each other and from said pins, said posts extending from said distal face a distance less than said pins and having substantially flat faces to limit penetration of said pins in the tissue.

28. A device for engaging tissue in the body as recited in claim 27 wherein said pins have lands thereon disposed a distance from said distal face the same as the length of said posts.

* * * * *

UNITED STATES PATENT AND TRADEMARK OFFICE
CERTIFICATE OF CORRECTION

PATENT NO. : 4,988,351

DATED : January 29, 1991

INVENTOR(S) : Leon E. Paulos et al

It is certified that error appears in the above-identified patent and that said Letters Patent is hereby corrected as shown below:

Column 1, line 60, after "of", insert --a--.

Column 2, line 4, after "including", insert --a--.

Column 6, line 37, after "lateral", insert --rim--.

Signed and Sealed this

Twenty-sixth Day of May, 1992

*Attest:*

DOUGLAS B. COMER

*Attesting Officer*     *Acting Commissioner of Patents and Trademarks*